US006762183B2

(12) United States Patent
Fischer et al.

(10) Patent No.: US 6,762,183 B2
(45) Date of Patent: Jul. 13, 2004

(54) ACTIVE SUBSTANCE COMBINATIONS HAVING INSECTICIDAL AND ACARICIDAL PROPERTIES

(75) Inventors: Reiner Fischer, Monheim (DE); Christoph Erdelen, Leichlingen (DE); Thomas Bretschneider, Lohmar (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/257,043

(22) PCT Filed: Mar. 29, 2001

(86) PCT No.: PCT/EP01/03602

§ 371 (c)(1),
(2), (4) Date: Oct. 7, 2002

(87) PCT Pub. No.: WO01/76369

PCT Pub. Date: Oct. 18, 2001

(65) Prior Publication Data

US 2003/0211944 A1 Nov. 13, 2003

(30) Foreign Application Priority Data

Apr. 11, 2000 (DE) ......................................... 100 17 881

(51) Int. Cl.$^7$ ...................... A10N 43/707; A10N 43/06; A10N 43/08; A10N 43/12; A10N 43/40; A10N 43/56; A10N 43/58; A10N 43/72

(52) U.S. Cl. ...................... 514/242; 514/114; 514/120; 514/121; 514/125; 514/126; 514/129; 514/131; 514/134; 514/139; 514/140; 514/247; 514/252; 514/336; 514/354; 514/357; 514/365; 514/369; 514/406; 514/407; 514/430; 514/431; 514/432; 514/433; 514/438; 514/439; 514/444; 514/445; 514/448; 514/449; 514/450; 514/451; 514/452; 514/459; 514/460; 514/461; 514/462; 514/463; 514/468; 514/469; 514/470; 514/471; 514/472; 514/473; 514/474; 514/475; 514/875; 514/919; 424/DIG. 10; 424/DIG. 11

(58) Field of Search .................. 514/114, 120, 514/121, 125, 126, 129–131, 134, 139, 140, 247, 252, 336, 354, 357, 365, 369, 406, 407, 430–433, 438, 439, 444, 445, 448, 449, 450, 451, 452, 459–463, 468–474, 475, 875, 919; 424/DIG. 10, DIG. 11

(56) References Cited

U.S. PATENT DOCUMENTS

| | | | |
|---|---|---|---|
| 3,264,177 A | 8/1966 | Kenaga | 167/30 |
| 4,053,634 A | 10/1977 | Bellina et al. | 424/312 |
| 4,055,661 A | 10/1977 | Bellina et al. | 424/311 |
| 4,070,481 A | 1/1978 | Bellina et al. | 424/311 |
| 4,082,848 A | 4/1978 | Bellina et al. | 424/273 R |
| 4,115,584 A | 9/1978 | Bellina et al. | 424/301 |
| 4,143,157 A | 3/1979 | Bellina et al. | 424/314 |
| 4,148,918 A | 4/1979 | Bellina et al. | 424/314 |
| 4,843,068 A | 6/1989 | Hamaguchi et al. | 514/63 |
| 4,962,126 A | 10/1990 | Drabek | 514/587 |
| 5,010,098 A | 4/1991 | Brown et al. | 514/426 |
| 5,310,938 A | 5/1994 | Brown et al. | 548/557 |
| 5,367,093 A | 11/1994 | Dekeyser et al. | 560/27 |
| 5,438,123 A | 8/1995 | Dekeyser et al. | 534/885 |
| 5,455,263 A | 10/1995 | Doscher et al. | 347/422 |
| 5,478,855 A | 12/1995 | Suzuki et al. | 514/374 |
| 5,536,746 A | 7/1996 | Dekeyser et al. | 514/468 |
| 5,610,122 A | 3/1997 | Fischer et al. | 647/251 |
| 5,683,965 A | 11/1997 | Bachmann et al. | 504/238 |
| 5,719,310 A | 2/1998 | Fischer et al. | 647/83 |
| 5,807,805 A | 9/1998 | Fischer et al. | 504/247 |
| 5,830,825 A | 11/1998 | Fischer et al. | 504/130 |
| 5,994,274 A | 11/1999 | Fischer et al. | 504/282 |
| 6,025,383 A | 2/2000 | Fischer et al. | 514/422 |
| 6,051,723 A | 4/2000 | Fischer et al. | 549/420 |
| 6,100,220 A | 8/2000 | Fischer et al. | 504/289 |
| 6,110,872 A | 8/2000 | Lieb et al. | 504/284 |
| 6,114,374 A | 9/2000 | Lieb et al. | 514/424 |
| 6,133,296 A | 10/2000 | Lieb et al. | 514/343 |
| 6,140,358 A | 10/2000 | Lieb et al. | 514/425 |
| 6,200,932 B1 | 3/2001 | Fischer et al. | 504/225 |
| 6,251,830 B1 | 6/2001 | Fischer et al. | 504/251 |
| 6,255,342 B1 | 7/2001 | Lieb et al. | 514/533 |
| 6,271,180 B2 | 8/2001 | Lieb et al. | 504/292 |
| 6,316,486 B1 | 11/2001 | Lieb et al. | 514/411 |
| 6,358,887 B1 | 3/2002 | Fischer et al. | 504/284 |
| 6,359,151 B2 | 3/2002 | Lieb et al. | 549/265 |
| 6,380,246 B1 | 4/2002 | Lieb et al. | 514/462 |
| 6,388,128 B1 | 5/2002 | Conrow | 560/76 |
| 6,417,370 B1 | 7/2002 | Lieb et al. | 548/408 |
| 6,451,843 B1 | 9/2002 | Lieb et al. | 514/422 |
| 6,458,965 B1 | 10/2002 | Lieb et al. | 548/408 |
| 6,469,196 B2 | 10/2002 | Fischer et al. | 560/105 |
| 6,486,343 B1 | 11/2002 | Lieb et al. | 560/39 |
| 2001/0004629 A1 | 6/2001 | Lieb et al. | 504/292 |
| 2002/0010204 A1 | 1/2002 | Lieb et al. | 514/424 |
| 2002/0022575 A1 | 2/2002 | Fischer et al. | 504/221 |

FOREIGN PATENT DOCUMENTS

| | | |
|---|---|---|
| DE | 528156 | 2/1993 |
| WO | 98/47368 | 10/1998 |
| WO | 99/16748 | 4/1999 |
| WO | 01/33966 | 5/2001 |

OTHER PUBLICATIONS

Cropu Abstract, accession No. 2001–88328, abstracting DE 19953775 (2001).*
BCPC Conf.—Pests & Diseases, vol. 1, (month unavailable) 2000, pp. 59–65, M. Morita et al, IKI–220, "A novel systemic aphicide".
Chem. Ind., 37, (month unavailable) 1985, pp. 730–732, H. R. Ungerer, "Schiffsfarben–eine Spezialitat der seenahen Lackindustrie".
Weeds, 15 (month unavailable) 1967, pp. 20–22, S. R. Colby, "Calculating Synergistic and Antagonistic Responses of Herbicide Combination".

* cited by examiner

Primary Examiner—John Pak
(74) Attorney, Agent, or Firm—Richard E. L. Henderson

(57) ABSTRACT

The invention relates to novel active compound combinations of certain cyclic ketoenols and certain active compounds that together have unexpectedly good insecticidal and acaricidal properties.

9 Claims, No Drawings

ACTIVE SUBSTANCE COMBINATIONS HAVING INSECTICIDAL AND ACARICIDAL PROPERTIES

This application is a 371 of PCT/EP01/03602, filed on Mar. 29, 2001.

The present invention relates to novel active compound combinations comprising known cyclic ketoenols on the one hand and other known insecticidally active compounds on the other hand and which are highly suitable for controlling animal pests such as insects and undesired acarids.

It is already known that certain cyclic ketoenols have insecticidal and acaricidal properties (EP-A-528 156). WO 95/01971, EP-A-647 637, WO 96/16061, WO 96/20196, WO 96/25395, WO 96/35664, WO 97/02243, WO 97/01535, WO 97/36868, WO 97/43275, WO 98/05638, WO 98/06721, WO 99/16748, WO 99/43649, WO 99/48869 and WO 99/55673 describe further ketoenols having insecticidal and acaricidal properties. The activity of these substances is good; however, at low application rates it is sometimes unsatisfactory.

Furthermore, it is already known that numerous heterocycles, organotin compounds, benzoylureas and pyrethroids have insecticidal and acaricidal properties (cf. WO 93-22 297, WO 93-10 083, DE-A 2 641 343, EP-A-347 488, EP-A-210 487, U.S. Pat. No. 3,264,177 and EP-A-234 045). However, the activity of these substances is not always satisfactory.

It has now been found that compounds of the formula (I)

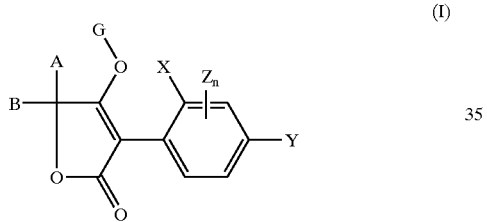

(I)

in which
X represents $C_1$–$C_6$-alkyl, halogen, $C_1$–$C_6$-alkoxy or $C_1$–$C_3$-halogenoalkyl,
Y represents hydrogen, $C_1$–$C_6$-alkyl, halogen, $C_1$–$C_6$-alkoxy or $C_1$–$C_3$-halogenoalkyl,
Z represents $C_1$–$C_6$-alkyl, halogen or $C_1$–$C_6$-alkoxy,
n represents a number from 0 to 3,
A represents hydrogen or in each case optionally halogen-substituted straight-chain or branched $C_1$–$C_{12}$-alkyl, $C_3$–$C_8$-alkenyl, $C_3$–$C_8$-alkinyl, $C_1$–$C_{10}$-alkoxy-$C_2$–$C_8$alkyl, $C_1$–$C_8$-polyalkoxy-$C_2$–$C_8$-alkyl, $C_1$–$C_{10}$-alkylthio-$C_2$–$C_8$-alkyl or cycloalkyl having 3–8 ring atoms which may be interrupted by oxygen and/or sulphur and represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy- or nitro-substituted phenyl or phenyl-$C_1$–$C_6$-alkyl,
B represents hydrogen, $C_1$–$C_6$-alkyl or $C_1$–$C_6$-alkoxy-$C_2$–$C_4$-alkyl
or in which
A and B together with the carbon atom to which they are attached form a saturated or unsaturated 3- to 8-membered ring which is optionally interrupted by oxygen and/or sulphur and optionally substituted by halogen, $C_1$–$C_6$-alkyl, $C_1$–$C_6$-alkoxy, $C_1$–$C_4$-halogenoalkyl, $C_1$–$C_4$-halogenoalkoxy, $C_1$–$C_4$-alkylthio or optionally substituted phenyl or is optionally benzo-fused,
G represents hydrogen (a) or represents a group

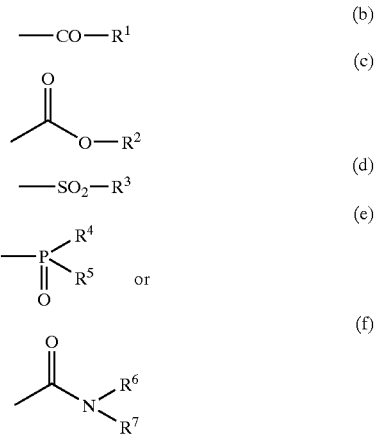

in which
$R^1$ represents in each case optionally halogen-substituted $C_1$–$C_{20}$-alkyl, $C_2$–$C_{20}$-alkenyl, $C_1$–$C_8$-alkoxy-$C_2$–$C_8$-alkyl, $C_1$–$C_8$-alkylthio-$C_2$–$C_8$-alkyl, $C_1$–$C_8$-polyalkoxy-$C_2$–$C_8$-alkyl or cycloalkyl having 3–8 ring atoms which may be interrupted by oxygen and/or sulphur atoms,
represents optionally halogen-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl,
represents optionally halogen-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl,
represents in each case optionally halogen- and/or $C_1$–$C_6$-alkyl-substituted pyridyl, pyrimidyl, thiazolyl or pyrazolyl,
represents optionally halogen- and/or $C_1$–$C_6$-alkyl-substituted phenoxy-$C_1$–$C_6$-alkyl,
$R^2$ represents in each case optionally halogen-substituted $C_1$–$C_{20}$-alkyl, $C_2$–$C_{20}$-alkenyl, $C_1$–$C_8$-alkoxy-$C_2$–$C_8$-alkyl or $C_1$–$C_8$-polyalkoxy-$C_2$–$C_8$-alkyl,
represents in each case optionally halogen-, nitro-, $C_1$–$C_6$-alkyl-, $C_1$–$C_6$-alkoxy- or $C_1$–$C_6$-halogenoalkyl-substituted phenyl or benzyl,
$R^3$ represents optionally halogen-substituted $C_1$–$C_8$-alkyl,
represents in each case optionally $C_1$–$C_4$-alkyl-, halogen-, $C_1$–$C_4$-halogenoalkyl-, $C_1$–$C_4$-alkoxy-, $C_1$–$C_4$-halogenoalkoxy-, nitro- or cyano-substituted phenyl or benzyl,
$R^4$ and $R^5$ independently of one another represent in each case optionally halogen-substituted $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkinylthio or $C_3$–$C_7$-cycloalkylthio, represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, phenoxy or phenylthio,
$R^6$ and $R^7$ independently of one another represent in each case optionally halogen-substituted $C_1$–$C_{10}$-alkyl, $C_1$–$C_{10}$-alkoxy, $C_1$–$C_8$-alkoxy-$C_1$–$C_8$-alkyl, represent optionally halogen-, $C_1$–$C_6$-halogenoalkyl-, $C_1$–$C_6$-alkyl- or $C_1$–$C_6$-alkoxy-substituted phenyl, represent optionally halogen-, $C_1$–$C_6$-alkyl-, $C_1$–$C_6$-halogenoalkyl- or $C_1$–$C_6$-alkoxy-substituted benzyl or together represent a 5- or 6-membered ring which is optionally interrupted by oxygen or sulphur and which may optionally be substituted by $C_1$–$C_6$-alkyl, and 1. amitraz

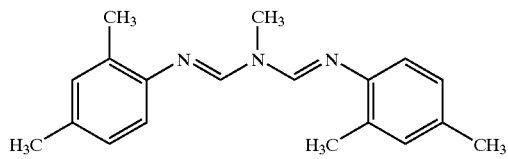

known from DE-A-2 061 132 and/or 2. buprofezin

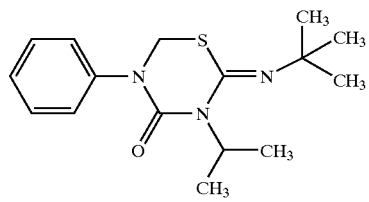

known from DE-A-2 824 126 and/or 3. triazamate

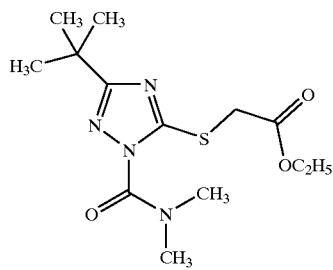

known from EP-A-213 718 and/or 4. pymetrozin or (pymetrozine)

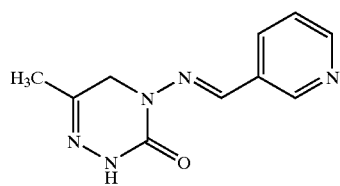

known from EP-A-3 14 615

5. pyriproxyfen

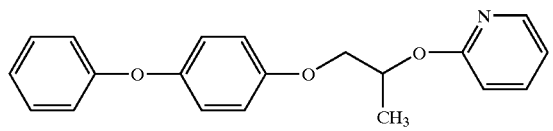

known from EP-A-128 648

6. IKI 220

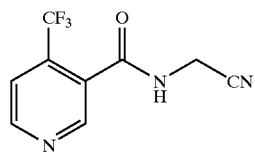

known from BCPC Conf.-Pests Dis. (2000), (Vol.1), 59 to 65 have very good insecticidal and acaricidal properties.

Surprisingly, the insecticidal and acaricidal action of the active compound combinations according to the invention considerably exceeds the total of the actions of the individual active compounds. A true synergistic effect which could not have been predicted exists, not just a complementation of action.

The active compound combinations according to the invention comprise, in addition to at least one active compound of the formula (I), at least one active compound of compounds 1 to 6.

Preference is given to active compound combinations comprising compounds of the formula (I)

in which

X represents $C_1$–$C_4$-alkyl, halogen, $C_1$–$C_4$-alkoxy or $C_1$–$C_2$-halogenoalkyl, Y represents hydrogen, $C_1$–$C_4$-alkyl, halogen, $C_1$–$C_4$-alkoxy or $C_1$–$C_2$-halogenoalkyl, Z represents $C_1$–$C_4$-alkyl, halogen or $C_1$–$C_4$-alkoxy, n represents 0 or 1, A and B together with the carbon atom to which they are attached form a saturated, optionally $C_1$–$C_4$-alkyl- or $C_1$–$C_4$-alkoxy-substituted 5- or 6-membered ring, G represents hydrogen (a) or represents the groups

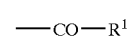 (b)

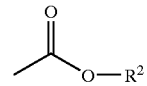 (c)

in which $R^1$ represents in each case optionally halogen-substituted $C_1$–$C_{16}$-alkyl, $C_2$–$C_{16}$-alkenyl, $C_1$–$C_6$-alkoxy-$C_2$–$C_6$-alkyl or cycloalkyl having 3–7 ring atoms which may be interrupted by 1 or 2 oxygen and/or sulphur atoms, represents optionally halogen-, nitro-, $C_1$–$C_4$-alkyl-, $C_1$–$C_4$-alkoxy-, $C_1$–$C_3$-halogenoalkyl- or $C_1$–$C_3$-halogenoalkoxy-substituted phenyl, $R^2$ represents in each case optionally halogen-substituted $C_1$–$C_{16}$-alkyl, $C_2$–$C_{16}$-alkenyl or $C_1$–$C_6$-alkoxy-$C_2$–$C_6$-alkyl, represents in each case optionally halogen-, nitro-, $C_1$–$C_4$-alkyl-, $C_1$–$C_4$-alkoxy- or $C_1$–$C_4$-halogenoalkyl-substituted phenyl or benzyl, and at least one active compound of compounds 1 to 6.

Particular preference is given to active compound combinations comprising the dihydrofuranone derivative of the formula (I-b-1)

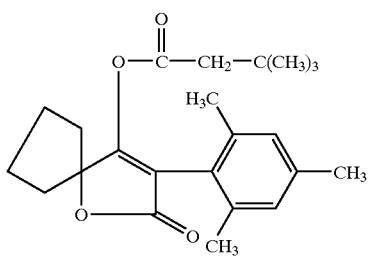

(I-b-1)

and at least one active compound of compounds 1 to 6.

In addition, the active compound combinations may also comprise other fungicidally, acaricidally or insecticidally active components which may be admixed.

If the active compounds are present in the active compound combinations according to the invention in certain weight ratios, the synergistic effect is particularly pronounced. However, the weight ratios of the active compounds in the active compound combinations may be varied within a relatively wide range. In general, the combinations according to the invention comprise active compounds of the formula (I) and the co-components in the preferred and particularly preferred mixing ratios indicated in the table below:

the mixing ratios are based on weight ratios. The ratio is to be understood as meaning active compound of the formula (I): co-component

| Co-component | Preferred mixing ratio | Particularly preferred mixing ratio |
|---|---|---|
| amitraz | 5:1 to 1:20 | 1:1 to 1:10 |
| buprofezin | 10:1 to 1:10 | 5:1 to 1:5 |
| pymetrozin | 10:1 to 1:10 | 5:1 to 1:5 |
| pyriproxyphen | 10:1 to 1:10 | 5:1 to 1:5 |
| triazamate | 10:1 to 1:10 | 5:1 to 1:5 |
| IKI 220 | 10:1 to 1:10 | 5:1 to 1:5 |

The active compound combinations according to the invention are suitable for controlling animal pests, preferably arthropods and nematodes, in particular insects and arachnids found in agriculture, in animal health, in forests, in the protection of stored products and materials and in the hygiene sector. They are active against normally sensitive and resistant species, and against all or individual developmental stages. The abovementioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus,* Scutigera spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus,* Gryllotalpa spp., *Locusta migratoria migratorioides,* Melanoplus spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, Reticulitermes spp.

From the order of the Phthiraptera, for example, *Pediculus humanus corporis,* Haematopinus spp., Linognathus spp., Trichodectes spp., Damalinia spp.

From the order of the Thysanoptera, for example, *Hercinothrips femoralis, Thrips tabaci, Thrips palmi, Frankliniella occidentalis.*

From the order of the Heteroptera, for example, Eurygaster spp., *Dysdercus intermedius, Piesma quadrata, Cimex lectularius, Rhodnius prolixus,* Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp., Psylla spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Mamestra brassicae, Panolis flammea,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana,* Cnaphalocerus spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis, Costelytra zealandica, Lissorhoptrus oryzophilus.*

From the order of the Hymenoptera, for example, Diprion spp., Hoplocampa spp., Lasius spp., *Monomorium pharaonis,* Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae, Tipula paludosa,* Hylemyia spp., Liriomyza spp.

From the order of the Siphonaptera, for example, *Xenopsylla cheopis,* Ceratophyllus spp.

From the class of the Arachnida, for example, *Scorpio maurus, Latrodectus mactans, Acarus siro,* Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Hemitarsonemus spp., Brevipalpus spp.

The plant-parasitic nematodes include, for example, Pratylenchus spp., *Radopholus similis, Ditylenchus dipsaci, Tylenchulus semipenetrans*, Heterodera spp., Globodera spp., Meloidogyne spp., Aphelenchoides spp., Longidorus spp., Xiphinema spp., Trichodorus spp., Bursaphelenchus spp.

The active compound combinations can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethyl-formamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in their commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Mixtures with other known active compounds such as herbicides or with fertilizers and growth regulators are also possible.

When used as insecticides, the active compound combinations according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound combinations are distinguished by an excellent residual action on wood and clay as well as good stability to alkali on limed substrates.

The active compound combinations according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the suborders Amblycerina and Ischnocerina, for example, Trimenopon spp., Menopon spp., Trinoton spp., Bovicola spp., Wemeckiella spp., Lepikentron spp., Damalina spp., Trichodectes spp., Felicola spp.

From the order Diptera and the suborders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp., Melophagus spp.

From the order of the Siphonapterida, for example, Pulex spp., Ctenocephalides spp., Xenopsylla spp., Ceratophyllus spp.

From the order of the Heteropterida, for example, Cimex spp., Triatoma spp., Rhodnius spp., Panstrongylus spp.

From the order of the Blattarida, for example, *Blatta orientalis, Periplaneta americana, Blattela germanica*, Supella spp.

From the subclass of the Acaria (Acarida) and the order of the Meta- and Mesostigmata, for example, Argas spp., Omithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Stemostoma spp., Varroa spp.

From the order of the Actinedida (Prostigmata) and Acaridida (Astigmata), for example, Acarapis spp., Cheyletiella spp., Omithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp., Laminosioptes spp.

The active compound combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compound combinations according to the invention.

The active compound combinations according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compound combinations can be applied as formulations (for example powders, emulsions, flowables) comprising the active compounds in an amount of 1 to 80% by weight, either directly or after 100- to 10,000-fold dilution, or they may be used as a chemical dip.

Moreover, it has been found that the active compound combinations according to the invention show a potent insecticidal action against insects which destroy industrial materials.

The following insects may be mentioned by way of example and with preference, but not by way of limitation:

Beetles such as

*Hylotrupes bajulus, Chlorophorus pilosis, Anobium punctatum, Xestobium rufovillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis*, Xyleborus spec., Tryptodendron spec., *Apate monachus, Bostrychus capucins, Heterobostrychus brunneus*, Sinoxylon spec., *Dinoderus minutus.*

Dermapterans such as

*Sirex juvencus, Urocerus gigas, Urocerus gigas taignus, Urocerus augur.*

Termites such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristle-tails such as *Lepisma saccharina.*

Industrial materials in the present context are understood as meaning non-living materials such as, preferably, polymers, adhesives, glues, paper and board, leather, wood, timber products and paints.

The material which is to be protected from insect attack is very especially preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compound combinations can be used as such, in the form of concentrates or generally customary formulations such as powders, granules, solutions, suspensions, emulsions or pastes.

The abovementioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of terpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the abovementioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the abovementioned organochemical solvents or diluents, emulsifiers and dispersants.

Particularly effective timber protection is achieved by industrial-scale impregnating processes, for example the vacuum, double-vacuum or pressure processes.

The active compound combinations according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example Ectocarpus sp. and Ceramium sp., fouling by sessile Entomostraka groups, which come under the generic term Cirripedia (*cirriped crustaceans*), is of particular importance.

Surprisingly, it has now been found that the active compound combinations according to the invention have an outstanding antifouling action.

Using the active compound combinations according to the invention, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as
2-tert-butylamino-4-cyclopropylamino-6-methylthio-1,3,5-triazine, dichlorophen, diuron, endothal, fentine acetate, isoproturon, methabenzthiazuron, oxyfluorfen, quinoclamine and terbutryn;

fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulfone, 2-(N,N-di-methylthiocarbamoyl-thio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl)-pyridine, 2,4,5,6-tetrachloroisophthalonitrile, tetramethylthiuram disulfide and 2,4,6-trichlorophenylmaleiimide.

The antifouling compositions used comprise the active compound combinations according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compound combinations are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests. They are active against sensitive and resistant species and against all developmental stages.

These pests include:

From the order of the Scorpionidea, for example, *Buthus occitanus*.

From the order of the Acarina, for example, *Argas persicus, Argas reflexus*, Bryobia ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, Aviculariidae, Araneidae.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus*, Polydesmus spp.

From the order of the Chilopoda, for example, Geophilus spp.

From the order of the Zygentoma, for example, Ctenolepisma spp., *Lepisma saccharina, Lepismodes inquilinus*.

From the order of the Blattaria, for example, *Blatta orientalies, Blattella germanica, Blattella asahinai, Leucophaea maderae*, Panchlora spp., Parcoblatta spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, Kalotermes spp., Reticulitermes spp.

From the order of the Psocoptera, for example, Lepinatus spp., Liposcelis spp.

From the order of the Coleptera, for example, Anthrenus spp., Attagenus spp., Dermestes spp., Latheticus oryzae, Necrobia spp., Ptinus spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus*, Anopheles spp., *Calliphora erythrocephala, Chrysozona pluvialis, Culex quinquefasciatus, Culex pipiens, Culex tarsalis*, Drosophila spp., *Fannia canicularis, Musca domestica*, Phlebotomus spp., *Sarcophaga carnaria*, Simulium spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis*, Paravespula spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant varieties protectable or not protectable by plant breeders' rights, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seed, also by applying one or more coats.

The good insecticidal and acaricidal action of the active compound combinations according to the invention can be seen from the examples which follow. While the individual active compounds show weaknesses in their action, the combinations show an action which exceeds a simple sum of actions.

A synergistic effect in insecticides and acaricides is always present when the action of the active compound combinations exceeds the total of the actions of the active compounds when applied individually.

The expected action for a given combination of two active compounds can be calculated as follows, using the formula of S. R. Colby, Weeds 15 (1967), 20–22:

If

X is the efficacy, expressed as % of the untreated control, when employing active compound A at an application rate of m g/ha or in a concentration of m ppm, Y is the efficacy, expressed as % of the untreated control, when employing active compound B at an application rate of n g/ha or in a concentration of n ppm and E is the efficacy, expressed as % of the untreated control, when employing active compounds A and B at application rates of m and n g/ha or in a concentration of m and n ppm, then $$E = X + Y - \frac{X \cdot Y}{100}$$

If the actual insecticidal kill rate exceeds the calculated value, the action of the combination is superadditive, i.e. a synergistic effect is present. In this case, the actually observed insecticidal kill rate must exceed the value calculated using the above formula for the expected insecticidal kill rate (E).

In this test, for example, the following active compound combinations in accordance with the present application exhibit a synergistically enhanced activity compared to the active compounds applied individually.

USE EXAMPLES

Bemisia Rest

| Solvent: | 7.5 parts by weight of dimethylformamide |
| Emulsifier: | 2.5 parts by weight of alkylaryl polyglycol ether |

To produce a suitable preparation of active compound, 1 part by weight of active compound is mixed with the stated amounts of solvent and emulsifier, and the concentrate is diluted with water to the desired concentration.

Cotton plants (*Gossypium hirsutum*) which are infested with eggs, larvae and pupae of the whitefly *Bemisia tabaci* are immersed in a preparation of active compound of the desired concentration.

After the desired period of time, the kill in % is determined 100% means that all animals have been killed; 0% means that none of the animals have been killed.

TABLE 1

| | plant-damaging insects Bemisia test | |
|---|---|---|
| Active components | Active compound Concentration in ppm | Kill rate in % after $10^d$ |
| Ex. (I-b-1) | 4 | 0 |
| Pymetrozin | 4 | 0 |
| Ex. (I-b-1) + pymetrozin (1:1) | 4 + 4 | found* calc.** 90 0 |

*found = activity found
**calc. = activity calculated using Colby's formula

TABLE 2

| | plant-damaging insects Bemisia test | |
|---|---|---|
| Active compounds | Active compound Concentration in ppm | Kill rate in % after $10^d$ |
| Ex. (I-b-1) | 20 | 80 |
| Pyriproxiphen | 20 | 0 |
| Ex. (I-b-1) + pyriproxiphen (1:1) According to the invention | 20 + 20 | found* calc.** 100 80 |

*found = activity found
**calc. = activity calculated using Colby's formula

What is claimed is:

1. A composition comprising a mixture of
(a) one or more compounds of the formula (I)

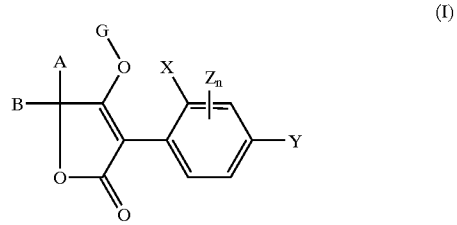

in which

X represents $C_1$–$C_6$-alkyl, halogen, $C_1$–$C_6$-alkoxy, or $C_1$–$C_3$-halogenoalkyl, Y represents hydrogen, $C_1$–$C_6$-alkyl, halogen, $C_1$–$C_6$-alkoxy, or $C_1$–$C_3$-halogenoalkyl, Z represents $C_1$–$C_6$-alkyl, halogen, or $C_1$–$C_6$-alkoxy, n represents a number from 0 to 3, A represents hydrogen; optionally halogen-substituted straight-chain or branched $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$-alkylthio-$C_2$–$C_8$-alkyl, or cycloalkyl having 3–8 ring atoms that may be interrupted by oxygen and/or sulphur; or optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, or nitro-substituted phenyl or phenyl-$C_1$–$C_6$-alkyl, B represents hydrogen, $C_1$–$C_6$-alkyl, or $C_1$–$C_6$-alkoxy-$C_2$–$C_4$-alkyl, or A and B together with the carbon atom to which they are attached form a saturated or unsaturated 3- to 8-membered ring that is optionally interrupted by oxygen and/or sulphur, optionally substituted by halogen, $C_1$–$C_6$-alkyl, $C_1$–$C_6$-alkoxy, $C_1$–$C_4$-halogenoalkyl, $C_1$–$C_4$-halogenoalkoxy, $C_1$–$C_4$-alkylthio, or optionally substituted phenyl, or optionally benzo-fused, G represents hydrogen (a) or a group

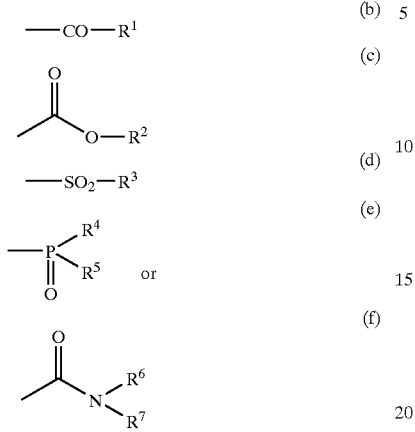

in which

R$^1$ represents (i) optionally halogen-substituted $C_1$–$C_{20}$-alkyl, $C_2$–$C_{20}$-alkenyl, $C_1$–$C_8$-alkoxy-$C_2$–$C_8$-alkyl, $C_1$–$C_8$-alkylthio-$C_2$–$C_8$-alkyl, $C_1$–$C_8$-polyalkoxy-$C_2$–$C_8$-alkyl, or cycloalkyl having 3 to 8 ring atoms that are optionally interrupted by oxygen and/or sulphur atoms, (ii) optionally halogen-, nitro-, $C_1$–$C_6$-alkyl-, $C_1$–$C_6$-alkoxy-, $C_1$–$C_6$-halogenoalkyl-, or $C_1$–$C_6$-halogenoalkoxy-substituted phenyl, (iii) optionally halogen-, $C_1$–$C_6$-alkyl-, $C_1$–$C_6$-alkoxy, $C_1$–$C_6$-halogenoalkyl-, or $C_1$–$C_6$-halogenoalkoxy-substituted phenyl-$C_1$–$C_6$-alkyl, (iv) optionally halogen- and/or $C_1$–$C_6$-alkyl-substituted pyridyl, pyrimidyl, thiazolyl, or pyrazolyl, or (v) optionally halogen- and/or $C_1$–$C_6$-alkyl-substituted phenoxy-$C_1$–$C_6$-alkyl, R$^2$ represents (i) optionally halogen-substituted $C_1$–$C_{20}$-alkyl, $C_2$–$C_{20}$-alkenyl, $C_1$–$C_8$-alkoxy-$C_2$–$C_8$-alkyl, or $C_1$–$C_8$-polyalkoxy-$C_2$–$C_8$alkyl, or (ii) optionally halogen-, nitro-, $C_1$–$C_6$-alkyl-, $C_1$–$C_6$-alkoxy-, or $C_1$–$C_6$-halogenoalkyl-substituted phenyl or benzyl, R$^3$ represents (i) optionally halogen-substituted $C_1$–$C_8$-alkyl or (ii) optionally $C_1$–$C_4$-alkyl-, halogen-, $C_1$–$C_4$-halogenoalkyl-, $C_1$–$C_4$-alkoxy-, $C_1$–$C_4$-halogenoalkoxy-, nitro-, or cyano-substituted phenyl or benzyl, R$^4$ and R$^5$ independently of one another represent (i) optionally halogen-substituted $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkinylthio, or $C_3$–$C_7$-cycloalkylthio or (ii) optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl-, or $C_1$–$C_4$-halogenoalkyl-substituted phenyl, phenoxy, or phenylthio, and R$^6$ and R$^7$ independently of one another represent (i) optionally halogen-substituted $C_1$–$C_{10}$-alkyl, $C_1$–$C_{10}$-alkoxy, $C_3$–$C_8$-alkenyl, or $C_1$–$C_8$-alkoxy-$C_1$–$C_8$-alkyl, (ii) optionally halogen-, $C_1$–$C_6$-halogenoalkyl-, $C_1$–$C_6$-alkyl-, or $C_1$–$C_6$-alkoxy-substituted phenyl, or (iii) optionally halogen-, $C_1$–$C_6$-alkyl-, $C_1$–$C_6$-halogenoalkyl-, or $C_1$–$C_6$-alkoxy-substituted benzyl; or R$^6$ and R$^7$ together represent a 5- or 6-membered ring that is optionally interrupted by oxygen or sulphur and is optionally substituted by $C_1$–$C_6$-alkyl, and (b) pymetrozine.

2. A composition according to claim 1 comprising a compound of the formula (I) in which X represents $C_1$–$C_4$-alkyl, halogen, $C_1$–$C_4$-alkoxy, or $C_1$–$C_2$-halogenoalkyl, Y represents hydrogen, $C_1$–$C_4$-alkyl, halogen, $C_1$–$C_4$-alkoxy, or $C_1$–$C_2$-halogenoalkyl, Z represents $C_1$–$C_4$-alkyl, halogen, or $C_1$–$C_4$-alkoxy, n represents 0 or 1, A and B together with the carbon atom to which they are attached form a saturated, optionally $C_1$–$C_4$-alkyl- or $C_1$–$C_4$-alkoxy-substituted 5- or 6-membered ring, and G represents hydrogen (a) or represents the groups

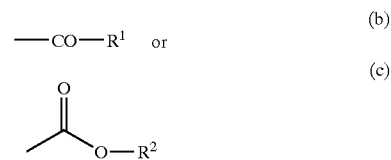

in which

R$_1$ represents (i) optionally halogen-substituted $C_1$–$C_{16}$-alkyl, $C_2$–$C_{16}$-alkenyl, $C_1$–$C_6$-alkoxy-$C_2$–$C_6$-alkyl, or cycloalkyl having 3 to 7 ring atoms that are optionally interrupted by 1 or 2 oxygen and/or sulphur atoms or (ii) optionally halogen-, nitro-, $C_1$–$C_4$-alkyl-, $C_1$–$C_4$-alkoxy-, $C_1$–$C_3$-halogenoalkyl-, or $C_1$–$C_3$-halogenoalkoxy-substituted phenyl, R$_2$ represents (i) optionally halogen-substituted $C_1$–$C_{16}$-alkyl, $C_2$–$C_{16}$-alkenyl, or $C_1$–$C_6$-alkoxy-$C_2$–$C_6$-alkyl or (ii) optionally halogen-, nitro-, $C_1$–$C_4$-alkyl-, $C_1$–$C_4$-alkoxy-, or $C_1$–$C_4$-halogenoalkyl-substituted phenyl or benzyl.

3. A composition according to claim 1, wherein the compound of the formula (I) is a compound of the formula (I-b-1)

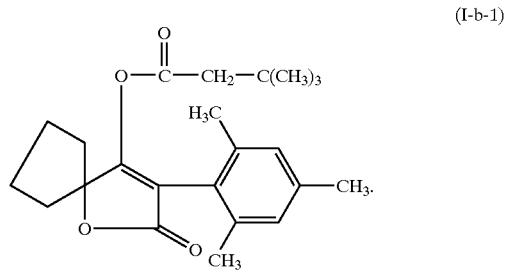

4. A method for controlling animal pests comprising allowing a mixture according to claim 1 to act on an animal pest and/or a habitat of an animal pest.

5. A method for controlling animal pests comprising allowing a mixture according to claim 2 to act on an animal pest and/or a habitat of an animal pest.

6. A method for controlling animal pests comprising allowing a mixture according to claim 3 to act on an animal pest and/or a habitat of an animal pest.

7. A process for preparing an insecticidal and acaricidal composition comprising mixing a mixture according to claim 1 with one or more extenders and/or surfactants.

8. A process for preparing an insecticidal and acaricidal composition comprising mixing a mixture according to claim 2 with one or more extenders and/or surfactants.

9. A process for preparing an insecticidal and acaricidal composition comprising mixing a mixture according to claim 3 with one or more extenders and/or surfactants.

* * * * *